(12) United States Patent
Yasuda et al.

(10) Patent No.: US 10,254,222 B2
(45) Date of Patent: Apr. 9, 2019

(54) GAS CONCENTRATION MEASUREMENT DEVICE

(71) Applicant: Murata Manufacturing Co., Ltd., Nagaokakyo-shi, Kyoto-fu (JP)

(72) Inventors: Masaaki Yasuda, Nagaokakyo (JP); Yoshinori Ikeda, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 126 days.

(21) Appl. No.: 15/384,362

(22) Filed: Dec. 20, 2016

(65) Prior Publication Data

US 2017/0102328 A1 Apr. 13, 2017

Related U.S. Application Data

(63) Continuation of application No. PCT/JP2015/066873, filed on Jun. 11, 2015.

(30) Foreign Application Priority Data

Jul. 3, 2014 (JP) .................................. 2014-137787

(51) Int. Cl.
*G01N 21/61* (2006.01)
*G01N 33/00* (2006.01)
*G01N 21/3504* (2014.01)

(52) U.S. Cl.
CPC ......... *G01N 21/61* (2013.01); *G01N 21/3504* (2013.01); *G01N 33/004* (2013.01); *G01N 2201/068* (2013.01); *G01N 2201/08* (2013.01)

(58) Field of Classification Search
None
See application file for complete search history.

(56) References Cited

U.S. PATENT DOCUMENTS

| 4,011,451 A | * | 3/1977 | Nelson | .................. G01N 21/05 250/343 |
| 4,181,437 A | * | 1/1980 | Rossiter | ................. G01N 21/03 250/343 |

(Continued)

FOREIGN PATENT DOCUMENTS

| JP | 2003-172700 A | 6/2003 |
| JP | 2003-215037 A | 7/2003 |

(Continued)

OTHER PUBLICATIONS

Official Communication issued in corresponding International Application PCT/JP2015/066873, dated Sep. 8, 2015.

(Continued)

*Primary Examiner* — Edwin C Gunberg
(74) *Attorney, Agent, or Firm* — Keating & Bennett, LLP

(57) ABSTRACT

A gas concentration measurement device includes a light source that emits infrared light, a detector that detects the infrared light through a band pass filter, and a waveguide including a wave-guiding portion that includes a tubular inner peripheral surface, an entrance that introduces the infrared light from the light source to the wave-guiding portion, and an exit that guides the infrared light that passes through the wave-guiding portion toward the detector. A portion or the entirety of the inner peripheral surface of the wave-guiding portion includes a tapered region that includes a cross section that decreases along a direction extending from the entrance to the exit. The waveguide reflects the infrared light that enters the wave-guiding portion to reduce energy of the infrared light that is obliquely incident on the band pass filter.

20 Claims, 5 Drawing Sheets

(56) References Cited

U.S. PATENT DOCUMENTS

| | | | |
|---|---|---|---|
| 4,736,103 A * | 4/1988 | Nelson ............... | G01N 21/3504 250/339.13 |
| 2003/0071218 A1 | 4/2003 | Nakamura et al. | |
| 2004/0064243 A1 | 4/2004 | Nakamura | |
| 2012/0250014 A1 | 10/2012 | Hayashi et al. | |
| 2014/0326889 A1 | 11/2014 | Sakamoto | |
| 2015/0316466 A1 | 11/2015 | Hirai et al. | |

FOREIGN PATENT DOCUMENTS

| | | |
|---|---|---|
| JP | 2004-117259 A | 4/2004 |
| JP | 2007-501404 A | 1/2007 |
| JP | 2010-223610 A | 10/2010 |
| JP | 2012-202918 A | 10/2012 |
| JP | 2013-092375 A | 5/2013 |
| JP | 2013-120153 A | 6/2013 |
| KR | 10-0791961 B1 | 1/2008 |
| WO | 01/27596 A1 | 4/2001 |
| WO | 2013/061817 A1 | 5/2013 |
| WO | 2014/083847 A1 | 6/2014 |

OTHER PUBLICATIONS

Official Communication issued in Japanese Patent Application No. 2016-531226, dated Jul. 4, 2017.
Official Communication issued in European Patent Application No. 15815028.4, dated Jan. 24, 2018.

* cited by examiner

GAS CONCENTRATION MEASUREMENT DEVICE

CROSS REFERENCE TO RELATED APPLICATIONS

This application claims the benefit of priority to Japanese Patent Application No. 2014-137787 filed on Jul. 3, 2014 and is a Continuation Application of PCT Application No. PCT/JP2015/066873 filed on Jun. 11, 2015. The entire contents of each application are hereby incorporated herein by reference.

BACKGROUND OF THE INVENTION

1. Field of the Invention

The present invention relates to an infrared-light-absorption gas concentration measurement device.

2. Description of the Related Art

Various types of gas concentration measurement devices for analyzing various types of exhaust, gas contained in the atmosphere, or gas contained in the air in a building have been developed. In particular, infrared-light-absorption gas concentration measurement devices are used to analyze sample gas because the sample gas absorbs infrared light in a specific wavelength range.

International Publication No. 01/27596, for example, discloses an infrared-light-absorption gas concentration measurement device. In the gas concentration measurement device disclosed in International Publication No. 01/27596, an anti-reflection film is applied to inner walls of an analysis chamber (sample cell) that defines a flow channel for the sample gas. Accordingly, the risk of the infrared light being incident on a band pass filter, which is provided on a surface of a detector, at an angle greater than a predetermined angle is somewhat reduced.

The anti-reflection film disclosed in International Publication No. 01/27596 must be made of a material including a reflectance close to zero. Thus, the material of the anti-reflection film is limited. If an inexpensive material including a reflectance that is not close to zero is used, the infrared light is reflected by the anti-reflection film such that the reflected infrared light is incident on the band pass filter at an angle greater than the predetermined angle. Thus, the transmission band of the band pass filter is shifted and the measurement accuracy of the gas concentration measurement device decreases.

Therefore, a gas concentration measurement device including a new structure that is able to be substituted for the anti-reflection film made of a specified material and that can reduce the risk of the reflected infrared light being incident on the band pass filter at an angle greater than the predetermined angle is needed.

SUMMARY OF THE INVENTION

Preferred embodiments of the present invention provide a gas concentration measurement device with significantly increased measurement accuracy.

A gas concentration measurement device according to a preferred embodiment of the present invention includes a light source that emits infrared light; a detector that detects the infrared light from the light source through a band pass filter; and a waveguide that includes a wave-guiding portion with a tubular inner peripheral surface, an entrance that is provided at one side of the wave-guiding portion and through which the infrared light from the light source is introduced, and an exit that is provided at the other side of the wave-guiding portion and guides the infrared light that passes through the wave-guiding portion toward the detector. A portion or an entirety of the inner peripheral surface of the wave-guiding portion includes a tapered region that includes a cross section that decreases along a direction extending from the entrance to the exit. The waveguide reflects the infrared light that enters the wave-guiding portion through the entrance in the tapered region, so that energy of the infrared light that is obliquely incident on the band pass filter is significantly reduced.

In a gas concentration measurement device according to a preferred embodiment of the present invention, preferably, the tapered region of the inner peripheral surface of the wave-guiding portion includes a truncated conical, substantially truncated conical, pyramidal, or substantially pyramidal portion including a perimeter that decreases along a direction extending from the entrance to the exit.

In a gas concentration measurement device according to a preferred embodiment of the present invention, preferably, an opening area of the entrance is greater than an opening area of the exit.

In a gas concentration measurement device according to a preferred embodiment of the present invention, preferably, the tapered region of the inner peripheral surface of the wave-guiding portion includes a first curved portion with a perimeter that decreases along a direction from the entrance to the exit.

In a gas concentration measurement device according to a preferred embodiment of the present invention, preferably, a length of the first curved portion in an axial direction of the wave-guiding portion is greater than, equal to, or substantially equal to about half a length of the wave-guiding portion in the axial direction of the wave-guiding portion.

In a gas concentration measurement device according to a preferred embodiment of the present invention, preferably, the inner peripheral surface of the wave-guiding portion includes a second curved portion with a perimeter that decreases along a direction from the exit to the entrance.

In a gas concentration measurement device according to a preferred embodiment of the present invention, preferably, the waveguide is made of a resin material.

According to preferred embodiments of the present invention, gas concentration measurement devices with significantly increased measurement accuracy are provided.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
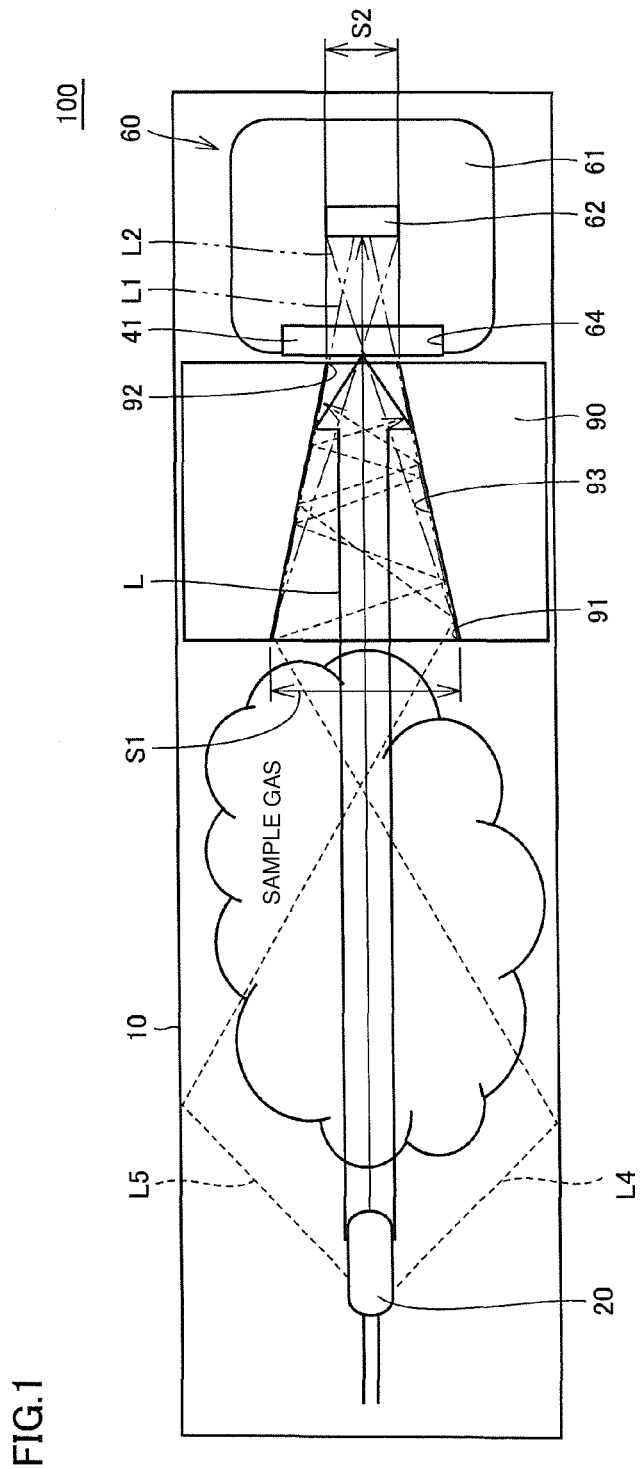
FIG. 1 is a schematic sectional view of a gas concentration measurement device according to a first preferred embodiment of the present invention.

Preferred embodiments of the present invention will be described in detail with reference to the drawings. In the preferred embodiments described below, components that are the same or similar are denoted by the same reference numerals in the drawings, and descriptions thereof will not be repeated.

First Preferred Embodiment

FIG. 1 is a schematic sectional view of a gas concentration measurement device according to the present preferred embodiment. The gas concentration measurement device according to the present preferred embodiment will be described with reference to FIG. 1.

As illustrated in FIG. 1, a gas concentration measurement device 100 according to the present preferred embodiment includes a sample cell 10, a light source 20, a band pass filter 41, a detector 60, and a waveguide 90. The gas concentration measurement device 100 measures a gas concentration in accordance with the absorbance of sample gas that flows through a space between the light source 20, which emits infrared light, and the detector 60, which includes a light-receiving portion 62 that receives the infrared light.

The sample cell 10 includes a sample-gas flow space and allows the sample gas to flow therethrough. For example, a sample-gas introduction hole (not shown) is connected to one end of the sample cell 10 (an end close to the light source 20), and a sample-gas discharge hole (not shown) is connected to the other end of the sample cell 10 (an end close to the detector 60). The sample gas introduced into the sample cell 10 through the sample-gas introduction hole is discharged through the sample-gas discharge hole.

The sample cell 10 contains the light source 20, the waveguide 90, the band pass filter 41, and the detector 60. The light source 20, the waveguide 90, the band pass filter 41, and the detector 60 are arranged, for example, in that order from one end of the sample cell 10 (from the left side in the figure).

The light source 20 emits infrared light. The light source 20 may be, for example, a filament lamp or an LED lamp that emits wide-band infrared light including the desired infrared light. A portion of the infrared light emitted from the light source 20 is absorbed depending on infrared light absorption wavelength characteristics of the sample gas. The sample gas is, for example, carbon dioxide, and the absorption band thereof is about 4.3 µm.

The waveguide 90 includes a wave-guiding portion 93 that includes a tubular inner peripheral surface; an entrance 91 that is provided at one end of the wave-guiding portion 93 and introduces the infrared light from the light source 20; and an exit 92 that is provided at the other end of the wave-guiding portion 93 and guides the infrared light that passes through the wave-guiding portion 93 toward the detector 60. The waveguide 90 guides the infrared light toward the detector 60 after a portion of the infrared light is absorbed by the sample gas.

The inner peripheral surface of the wave-guiding portion 93 includes a tapered region that includes a cross-sectional area that decreases from the entrance 91 toward the exit 92. The tapered region includes a truncated conical, substantially truncated conical, pyramidal, or substantially pyramidal shape with a circumference that decreases from the entrance 91 toward the exit 92. The truncated conical, substantially truncated conical, pyramidal, or substantially pyramidal shape includes a truncated conical or substantially truncated conical shape and a truncated polygonal pyramidal or substantially truncated polygonal pyramidal shape.

The waveguide 90 may be made of a resin material, such as acrylonitrile butadiene styrene copolymer synthetic resin (ABS resin) or polycarbonate resin (PC resin). In particular, the waveguide 90 is preferably made of a resin material including a reflectance of about 20% or less in the infrared wavelength range, for example.

The band pass filter 41 is provided at an end of the detector 60 that is adjacent to the waveguide 90. The band pass filter 41 is securely fitted in a recess 64 provided in a surface of the detector 60 that faces the waveguide 90.

The band pass filter 41 transmits the infrared light in an absorption band of the sample gas to be detected. Thus, only the infrared light including a desired wavelength band reaches the detector 60.

The detector 60 may be an infrared light detector, such as a thermopile or a bolometer. The detector 60 includes a main portion 61, a light-receiving portion 62, and the recess 64. The light-receiving portion 62 is embedded in the main portion 61. The light-receiving portion 62 receives the infrared light guided out of the exit 92 of the waveguide 90 through the band pass filter 41.

The detector 60 is electrically connected to a signal processing circuit board (not shown). The detector 60 outputs an output signal to the signal processing circuit board based on the infrared light received by the light-receiving portion 62. The signal processing circuit board calculates the concentration of the sample gas based on the output signal.

The infrared light incident on the band pass filter 41 will now be described. In general, the transmission band of the band pass filter 41 shifts toward the short-wavelength side of the infrared light as the incident angle of the infrared light increases. The measurement accuracy of the gas concentration measurement device decreases when the transmission band varies. Therefore, when gas concentration is measured, the incident angle of the infrared light incident on the band pass filter 41 is preferably small.

In the present preferred embodiment, the waveguide 90 is provided to significantly reduce or prevent the influence on the measurement accuracy of the infrared light with a large incident angle on the band pass filter 41 located in the transmitting position.

The infrared light that linearly travels through the region that is equal or substantially equal to the logical sum of the region surrounded by the outermost rays of infrared light L1 and the region surrounded by the outermost rays of infrared light L2 (for example, arrow L in FIG. 1) mainly reaches the light-receiving portion 62 through the band pass filter 41. The infrared light L1 is light including a truncated conical, substantially truncated conical, pyramidal, or substantially pyramidal shape that linearly travels along the peripheral surface of the wave-guiding portion 93 toward the detector 60. The infrared light L2 is light including two truncated cone or substantially truncated cone shapes obtained by rotating, for example, a ray of light that linearly travels from the bottom end of the entrance 91 of the waveguide 90 in FIG. 1 to the top end of the light-receiving portion 62 in FIG. 1, approximately one turn along the opening shape of the entrance 91.

The infrared light that linearly travels through the region that is or is substantially the logical sum of the region surrounded by the outermost rays of the infrared light L1 and the region surrounded by the outermost rays of the infrared light L2 passes through the band pass filter 41 at a small angle.

Infrared light L4 and infrared light L5 enter the wave-guiding portion 93 through the entrance 91 at a large angle with respect to the axial direction of the wave-guiding portion 93. The infrared light L4 and the infrared light L5 travel toward the detector 60 while being reflected by the inner peripheral surface of the wave-guiding portion 93 a plurality of times.

If the reflectance of the wave-guiding portion 93 is about 100%, the infrared light L4 and the infrared light L5 may be incident on the band pass filter 41 at a large incident angle.

In the present preferred embodiment, the waveguide 90 is preferably made of a resin material including a reflectance of about 20% or less. Therefore, the infrared light L4 and the infrared light L5 are absorbed and attenuated by being repeatedly reflected in the wave-guiding portion 93. For example, when the reflectance of the material is about 10%, the attenuation effect obtained when the infrared light is reflected five times is similar to that obtained when the infrared light is reflected once by a component including a reflectance of about 0.001%. The number of times the infrared light L4 and the infrared light L5 are reflected is able to be significantly increased by setting an opening area S1 of the entrance 91 of the waveguide 90 to be greater than an opening area S2 of the exit 92 and defining the wave-guiding portion 93 to include a tapered region.

Thus, the waveguide 90 repeatedly reflects the infrared light that has entered the wave-guiding portion 93 through the entrance 91 in the tapered region, thus significantly reducing the energy of the infrared light that is obliquely incident on the band pass filter 41. Accordingly, the measurement accuracy of the gas concentration measurement device is significantly increased.

As described above, in the gas concentration measurement device 100 according to the present preferred embodiment, since the waveguide 90 is provided, the energy of the obliquely incident infrared light is significantly reduced. Therefore, the measurement accuracy of the gas concentration measurement device 100 is significantly increased.

Although the sample gas is carbon dioxide in the present preferred embodiment, the sample gas is not so limited, and alternatively may be, for example, carbon monoxide, $CH_4$, or $NO_x$.

Second Preferred Embodiment

Figure 2:
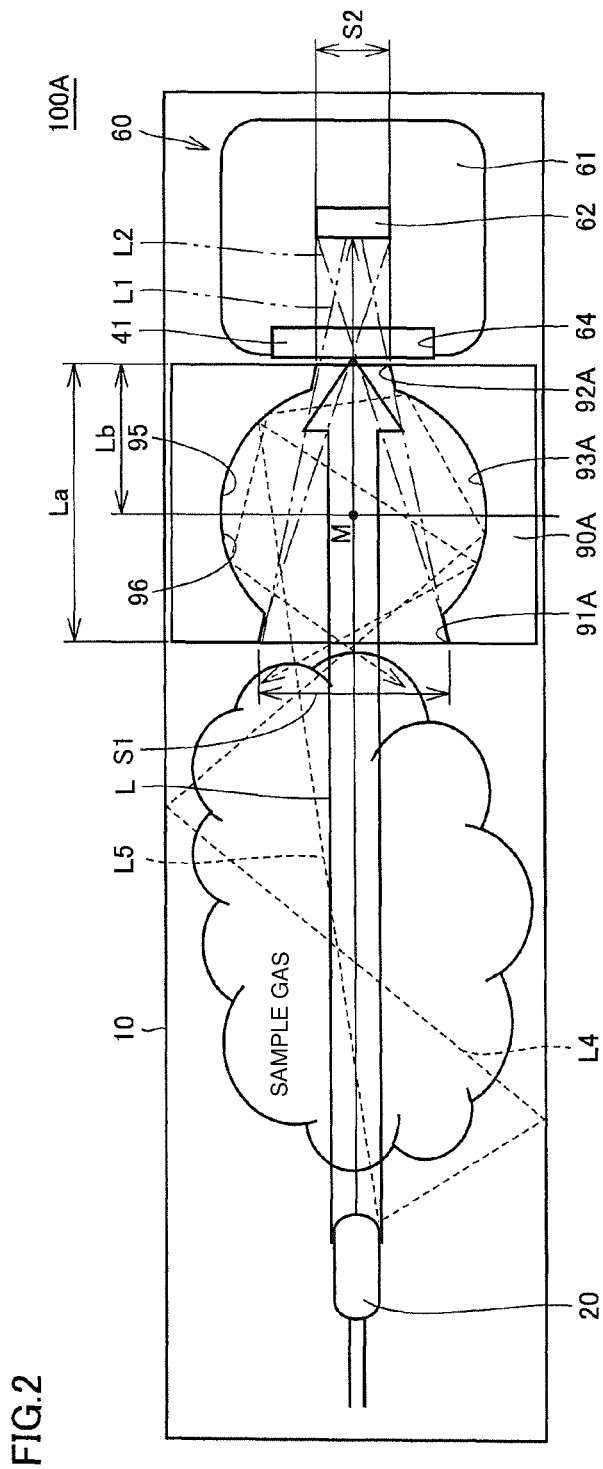
FIG. 2 is a schematic sectional view of a gas concentration measurement device according to a second preferred embodiment of the present invention.

FIG. 2 is a schematic sectional view of a gas concentration measurement device according to the present preferred embodiment. A gas concentration measurement device 100A according to the present preferred embodiment will be described with reference to FIG. 2.

As illustrated in FIG. 2, the gas concentration measurement device 100A according to the present preferred embodiment includes a waveguide 90A including a wave-guiding portion 93A that includes a shape that differs from that in the gas concentration measurement device 100 according to the first preferred embodiment. Other structures are substantially the same as those in the first preferred embodiment.

An opening area S1 of an entrance 91A of the waveguide 90A, is greater than an opening area S2 of an exit 92A of the waveguide 90A. The internal shape of the wave-guiding portion 93A preferably is partially spherical or substantially partially spherical. A portion of the inner peripheral surface of the wave-guiding portion 93A that defines a portion of a spherical or substantially spherical surface is located between the entrance 91A and the exit 92A.

The portion that defines a portion of the spherical or substantially spherical surface includes a first spherical surface portion 95, which extends toward the exit 92A from a boundary at or substantially at the center M of the sphere, and a second spherical surface portion 96, which extends toward the entrance 91A from the boundary at or substantially at the center M. The region from the first spherical surface portion 95 to the exit 92A corresponds to a tapered region including a cross-sectional area that decreases along the direction extending from the entrance 91A to the exit 92A, and also corresponds to a first curved or substantially curved portion including a circumference that decreases along the direction extending from the entrance 91A to the exit 92A. The second spherical surface portion 96 corresponds to a second curved or substantially curved portion including a circumference that decreases along the direction extending from the exit 92A to the entrance 91A.

When the wave-guiding portion 93A includes the above-described shape, the infrared light that linearly travels through the region that is or is substantially the logical sum of the region surrounded by the outermost rays of infrared light L1 and the region surrounded by the outermost rays of infrared light L2 (for example, arrow L in FIG. 2) mainly reaches the light-receiving portion 62. The infrared light L1 is light including a truncated conical, substantially truncated conical, pyramidal, or substantially pyramidal shape that linearly travels along the peripheral surfaces of the entrance 91A and the exit 92A toward the detector 60. The infrared light L2 is similar to that in the first preferred embodiment.

Infrared light L4 and infrared light L5 that enter the wave-guiding portion 93A through the entrance 91A at a large angle with respect to the axial direction of the wave-guiding portion 93A is reflected by the first spherical surface portion 95 and the second spherical surface portion 96 a plurality of times and emitted from the entrance 91A.

The infrared light L4 and the infrared light L5 emitted from the entrance 91A is not incident on the band pass filter 41. To increase the number of times the light is reflected by the wave-guiding portion 93A, the distance Lb from the first spherical surface portion 95 to the exit 92A in the axial direction of the wave-guiding portion 93A is preferably greater than, equal to, or substantially equal to about half the length La of the waveguide 90.

Thus, in the present preferred embodiment, the energy of the infrared light that is obliquely incident on the band pass filter 41 is significantly reduced, and a portion of the obliquely incident infrared light is emitted from the entrance 91A. Accordingly, the measurement accuracy of the gas concentration measurement device 100A is significantly increased.

Third Preferred Embodiment

Figure 3:
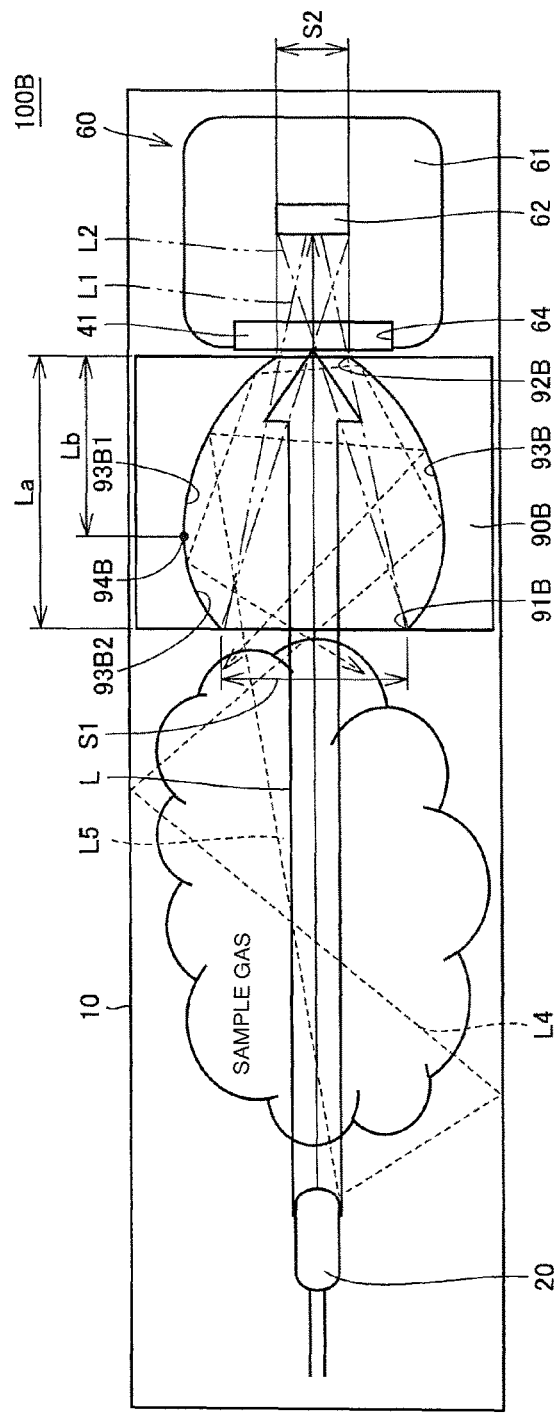
FIG. 3 is a schematic sectional view of a gas concentration measurement device according to a third preferred embodiment of the present invention.

FIG. 3 is a schematic sectional view of a gas concentration measurement device according to the present preferred embodiment. A gas concentration measurement device 100B according to the present preferred embodiment will be described with reference to FIG. 3.

As illustrated in FIG. 3, the gas concentration measurement device 100B according to the present preferred embodiment includes a waveguide 90B including a wave-guiding portion 93B with a shape that differs from that in the gas concentration measurement device 100 according to the first preferred embodiment. Other structures are substantially the same as those in the first preferred embodiment.

An opening area S1 of an entrance 91B of the waveguide 90B is greater than an opening area S2 of an exit 92B of the waveguide 90B. The internal shape of the wave-guiding portion 93B includes a first curved portion 93B1 and a second curved portion 93B2. The wave-guiding portion 93B includes a maximum circumference portion 94B. The maximum circumference portion 94B is located between the entrance 91B and the exit 92B.

The first curved portion 93B1 defines the internal shape of the wave-guiding portion 93B in a region that extends from the maximum circumference portion 94B to the exit 92B. The first curved portion 93B1 includes a circumference that decreases along the direction extending from the entrance 91B to the exit 92B.

The second curved portion 93B2 defines the internal shape of the wave-guiding portion 93B in a region that extends from the maximum circumference portion 94B to the entrance 91B. The second curved portion 93B2 includes a circumference that decreases along the direction extending from the exit 92B to the entrance 91B.

The infrared light that linearly travels through the region that is equal to or substantially equal to the logical sum of the region surrounded by the outermost rays of infrared light L1 and the region surrounded by the outermost rays of infrared light L2 mainly reaches the light-receiving portion 62. The infrared light L1 is light including a truncated conical, substantially truncated conical, pyramidal, or substantially pyramidal shape that linearly travels along the peripheral edges of the entrance 91B and the exit 92B toward the detector 60. The infrared light L2 is similar to that in the first preferred embodiment.

The length Lb of the first curved portion 93B1 in the axial direction of the waveguide 90B is preferably greater than, equal to, or substantially equal to about half the length La of the waveguide 90B in the axial direction. When this length relationship is satisfied, infrared light L4 and infrared light L5, which enter through the entrance 91B at a large angle with respect to the axial direction of the wave-guiding portion 93B, are reflected a plurality of times in the first curved portion 93B1 and the second curved portion 93B2 and emitted from the entrance 91B.

Accordingly, in the present preferred embodiment, the energy of the infrared light that is obliquely incident on the band pass filter 41 is reliably reduced by a significant amount. As a result, the measurement accuracy of the gas concentration measurement device 100B is significantly increased.

Fourth Preferred Embodiment

Figure 4:
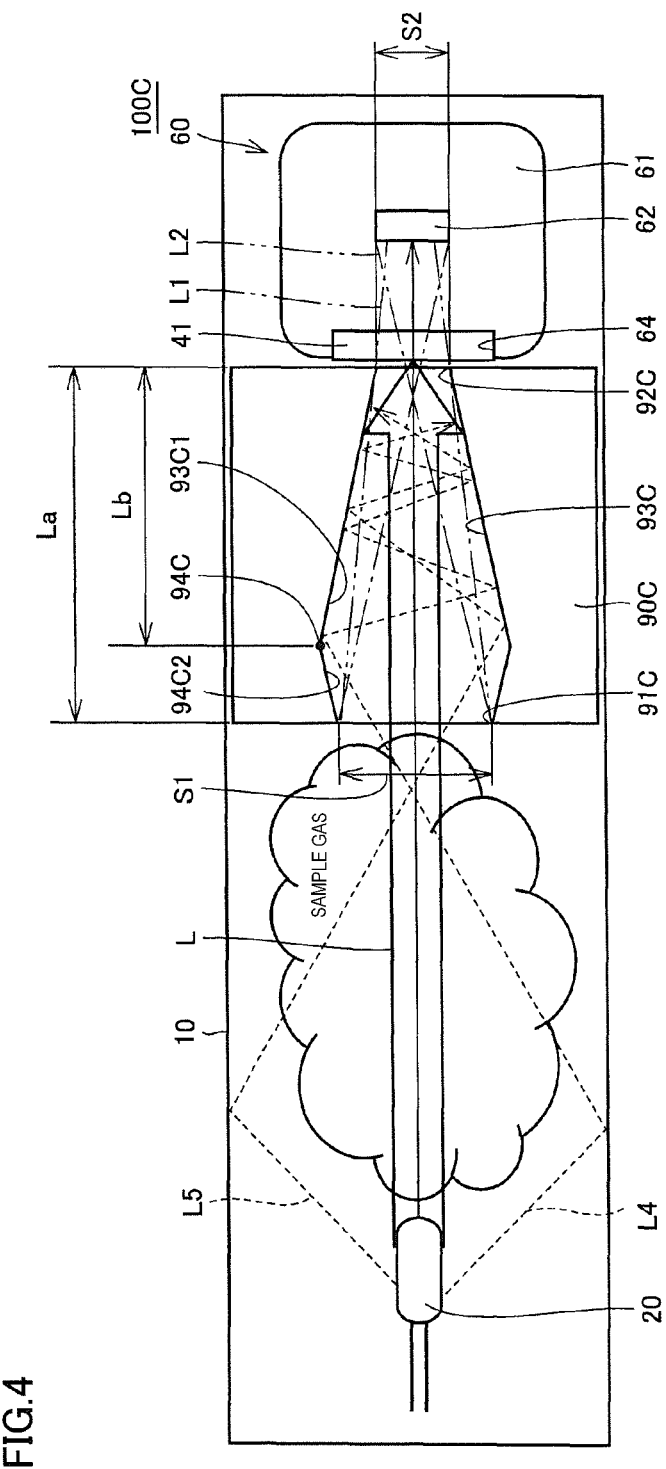
FIG. 4 is a schematic sectional view of a gas concentration measurement device according to a fourth preferred embodiment of the present invention.

FIG. 4 is a schematic sectional view of a gas concentration measurement device according to the present preferred embodiment. A gas concentration measurement device 100C according to the present preferred embodiment will be described with reference to FIG. 4.

As illustrated in FIG. 4, the gas concentration measurement device 100C according to the present preferred embodiment includes a waveguide 90C including a wave-guiding portion 93C with a shape that differs from that in the gas concentration measurement device 100 according to the first preferred embodiment. Other structures are substantially the same as those in the first preferred embodiment.

In the waveguide 90C, an opening area S1 of an entrance 91C is greater than an opening area S2 of an exit 92C. The internal shape of the wave-guiding portion 93C includes a first truncated conical or pyramidal portion 93C1 and a second truncated conical or pyramidal portion 93C2. The first and second truncated conical or pyramidal portions 93C1 and 93C2 each include a truncated conical, substantially truncated conical, pyramidal, or substantially pyramidal shape. The wave-guiding portion 93C includes a maximum circumference portion 94C. The maximum circumference portion 94C is located between the entrance 91C and the exit 92C.

The first truncated conical or pyramidal portion 93C1 defines the internal shape of the wave-guiding portion 93C in a region that extends from the maximum circumference portion 94C to the exit 92C. The first truncated conical or pyramidal portion 93C1 includes a circumference that decreases along the direction extending from the entrance 91C to the exit 92C.

The second truncated conical or pyramidal portion 93C2 defines the internal shape of the wave-guiding portion 93C in a region that extends from the maximum circumference portion 94C to the entrance 91C. The second truncated conical or pyramidal portion 93C2 includes a circumference that decreases along the direction extending from the exit 92C to the entrance 91C.

The infrared light that linearly travels through the region that is equal to or substantially equal to the logical sum of the region surrounded by the outermost rays of infrared light L1 and the region surrounded by the outermost rays of infrared light L2 mainly reaches the light-receiving portion 62. The infrared light L1 is light including a truncated conical, substantially truncated conical, pyramidal, or substantially pyramidal shape that linearly travels along the peripheral edges of the entrance 91C and the exit 92C toward the detector 60. The infrared light L2 is similar to that in the first preferred embodiment.

The length Lb of the first truncated conical or pyramidal portion 93C1 in the axial direction of the waveguide 90C is preferably greater than, equal to, or substantially equal to about half the length La of the waveguide 90C in the axial direction. When this length relationship is satisfied, infrared light L4, for example, which enters through the entrance 91C at a large angle with respect to the axial direction of the wave-guiding portion 93C, is reflected a plurality of times in the first truncated conical or pyramidal portion 93C1 and the second truncated conical or pyramidal portion 93C2.

Accordingly, in the gas concentration measurement device 100C according to the present preferred embodiment, the energy of the infrared light that is obliquely incident on the band pass filter 41 is reliably reduced by a significant amount. As a result, the measurement accuracy of the gas concentration measurement device is significant increased.

Fifth Preferred Embodiment

Figure 5:
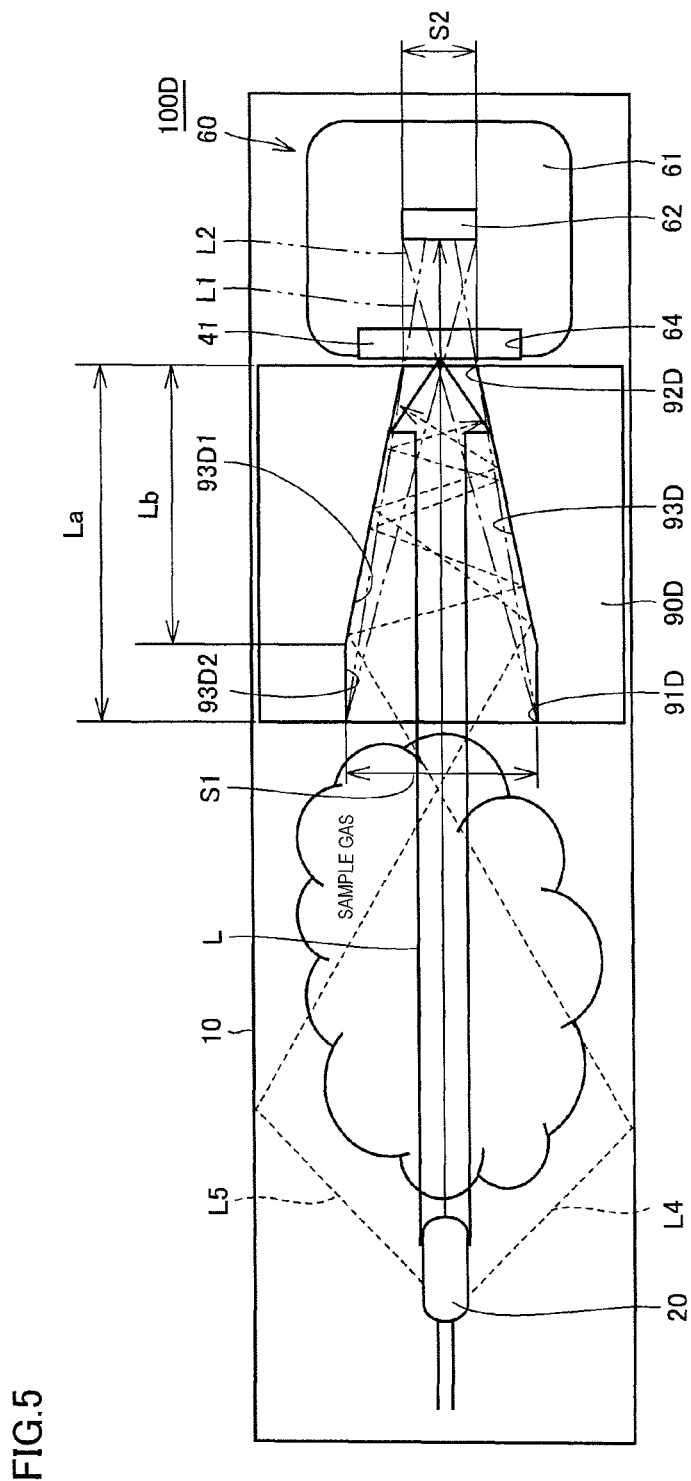
FIG. 5 is a schematic sectional view of a gas concentration measurement device according to a fifth preferred embodiment of the present invention.

FIG. 5 is a schematic sectional view of a gas concentration measurement device according to the present preferred embodiment. A gas concentration measurement device 100D according to the present preferred embodiment will be described with reference to FIG. 5.

As illustrated in FIG. 5, the gas concentration measurement device 100D according to the present preferred embodiment includes a waveguide 90D including a wave-guiding portion 93D with a shape that differs from that in the gas concentration measurement device 100C according to the fourth preferred embodiment.

An opening area S1 of an entrance 91D of the waveguide 90D is greater than an opening area S2 of an exit 92D of the waveguide 90D. The internal shape of the wave-guiding portion 93D includes a truncated conical or pyramidal portion 93D1 and a columnar portion 93D2. The shape of the truncated conical or pyramidal portion 93D1 is substantially the same as that of the first truncated conical or pyramidal portion 93C1 according to the fourth preferred embodiment. The truncated columnar portion 93D2 includes a columnar or substantially columnar shape. The relationship between the length of the truncated conical or pyramidal portion 93D1 and the length of the waveguide 90D is also similar to the relationship between the length of the first truncated conical or pyramidal portion 93C1 and the length of the waveguide 90C according to the fourth preferred embodiment.

The circumference of the columnar portion 93D2 is constant or substantially constant over a region that extends from the entrance 91D to the upstream end of the truncated conical or pyramidal portion 93D1. The circumference of the columnar portion 93D2 is equal or substantially equal to the maximum circumference of the truncated conical or pyramidal portion 93D1.

Infrared light L4 and infrared light L5, which enter through the entrance 91D at a large angle with respect to the axial direction of the wave-guiding portion 93D, is reflected a plurality of times in the truncated conical or pyramidal portion 93D1 and the columnar portion 93D2.

Accordingly, in the gas concentration measurement device 100D according to the present preferred embodiment, the energy of the infrared light that is obliquely incident on the band pass filter 41 is reliably reduced by a substantial amount. As a result, the measurement accuracy of the gas concentration measurement device is significantly increased.

In the present preferred embodiment, the columnar portion 93D2 is adjacent to the entrance 91D, and the truncated conical or pyramidal portion 93D1 is adjacent to the exit 92D. However, the arrangement of the truncated conical or pyramidal portion 93D1 and the columnar portion 93D2 is not so limited, and the columnar portion 93D2 may alternatively be adjacent to the exit 92D while the truncated conical or pyramidal portion 93D1 is alternatively adjacent to the entrance 91D. In this alternative arrangement, the circumference of the columnar portion 93D2 is preferably set to the minimum circumference of the truncated conical or pyramidal portion 93D1.

In the above-described second preferred embodiment, a portion that connects the entrance 91A to the upstream end of the second spherical surface portion 96 (first connecting portion) and a portion that connects the downstream end of the first spherical surface portion 95 to the exit 92A (second connecting portion) include circumferences that decrease along the direction extending from the entrance 91A to the exit 92A. However, the first and second connecting portions are not so limited, and at least one of the first and second connecting portions may include a columnar or substantially columnar shape with a constant or substantially constant circumference.

In the above-described third preferred embodiment, the second curved portion 93B2 extends from the entrance 91B to the maximum circumference portion 94B. However, the second curved portion 93B2 may be replaced by a columnar or substantially columnar portion including a circumference that is constant or substantially constant over a region that extends from the entrance 91B to the maximum circumference portion 94B.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A gas concentration measurement device comprising:
a light source that emits infrared light;
a detector that detects the infrared light from the light source through a band pass filter; and
a waveguide including a wave-guiding portion with a tubular inner peripheral surface, an entrance at one side of the wave-guiding portion and through which the infrared light from the light source is introduced, and an exit at the other side of the wave-guiding portion and guides the infrared light that passes through the wave-guiding portion toward the detector; wherein
a portion or an entirety of the inner peripheral surface of the wave-guiding portion includes a tapered region with a cross section that decreases along a direction extending from the entrance to the exit;
the waveguide reflects the infrared light that enters the wave-guiding portion through the entrance in the tapered region to reduce energy of the infrared light that is obliquely incident on the band pass filter; and
when viewed along a direction of the infrared light from the light source to the detector, the waveguide which reflects the infrared light is located in front of the band pass filter.

2. The gas concentration measurement device according to claim 1, wherein the tapered region of the inner peripheral surface of the wave-guiding portion includes a first truncated conical, substantially conical, pyramidal, or substantially pyramidal portion that includes a perimeter that decreases along the direction extending from the entrance to the exit.

3. The gas concentration measurement device according to claim 2, wherein the inner peripheral surface of the wave-guiding portion further includes a second truncated conical, substantially conical, pyramidal, or substantially pyramidal portion that includes a perimeter that decreases along a direction extending from the exit to the entrance.

4. The gas concentration measurement device according to claim 1, wherein an opening area of the entrance is greater than an opening area of the exit.

5. The gas concentration measurement device according to claim 1, wherein the tapered region of the inner peripheral surface of the wave-guiding portion includes a first curved portion that includes a perimeter that decreases along the direction extending from the entrance to the exit.

6. The gas concentration measurement device according to claim 5, wherein a length of the first curved portion in an axial direction of the wave-guiding portion is greater than, equal to, or substantially equal to about half a length of the wave-guiding portion in the axial direction of the wave-guiding portion.

7. The gas concentration measurement device according to claim 6, wherein the length of the first curved portion in the axial direction of the wave-guiding portion is greater than half of the length of the wave-guiding portion in the axial direction of the wave-guiding portion.

8. The gas concentration measurement device according to claim 6, wherein the length of the first curved portion in the axial direction of the wave-guiding portion is equal to or substantially equal to about half of the length of the wave-guiding portion in the axial direction of the wave-guiding portion.

9. The gas concentration measurement device according to claim 5, wherein the inner peripheral surface of the wave-guiding portion includes a second curved portion that includes a perimeter that decreases along a direction from the exit to the entrance.

10. The gas concentration measurement device according to claim 9, wherein
the waveguide includes a portion that connects the entrance of the waveguide to an upstream end of the second curved portion of the wave-guiding portion; and
the portion of the waveguide includes a circumference that decreases along the direction extending from the entrance of the waveguide to the exit of the waveguide, or a columnar or substantially columnar shape with a constant or substantially constant circumference.

11. The gas concentration measurement device according to claim 5, wherein
the waveguide includes a portion that connects a downstream end of the first curved portion to the exit of the waveguide; and
the portion of the waveguide includes a circumference that decreases along the direction extending from the entrance of the waveguide to the exit of the waveguide, or a columnar or substantially columnar shape with a constant or substantially constant circumference.

12. The gas concentration measurement device according to claim 1, wherein the waveguide is made of a resin material.

13. The gas concentration measurement device according to claim 1, wherein the light source, the waveguide, the band pass filter, and the detector are linearly disposed in that order.

14. The gas concentration measurement device according to claim 1, wherein the entirety of the inner peripheral surface of the wave-guiding portion includes the tapered region that includes the cross section that decreases along the direction extending from the entrance to the exit.

15. The gas concentration measurement device according to claim 1, wherein the tapered region of the wave-guiding portion is provided in only the portion of the inner peripheral surface of the wave-guiding portion.

16. The gas concentration measurement device according to claim 15, wherein
the waveguide includes a columnar portion at the entrance or the exit; and
a circumference of the columnar portion is equal or substantially equal to a minimum circumference of the tapered region of the wave-guiding portion or a maximum circumference of the tapered region of the wave-guiding portion.

17. The gas concentration measurement device according to claim 1, wherein the waveguide is made of a resin material including a reflectance of about 20% or less in the infrared wavelength range.

18. The gas concentration measurement device according to claim 1, wherein the waveguide is made of a resin material including a reflectance of about 10% in the infrared wavelength range.

19. The gas concentration measurement device according to claim 1, wherein a portion of the infrared light that enters the wave-guiding portion is reflected by the inner peripheral surface of the wave-guiding portion a plurality of times and emitted from the entrance.

20. The gas concentration measurement device according to claim 19, wherein the portion of the infrared light that is reflected by the inner peripheral surface of the wave-guiding portion is a portion of the energy of the infrared light that is obliquely incident on the band pass filter.

* * * * *